United States Patent [19]

Dorn et al.

[11] Patent Number: 4,753,947

[45] Date of Patent: Jun. 28, 1988

[54] CERTAIN FUNGICIDAL ALPHABENZYL-3-PYRIDYLMETHANOL, THE CORRESPONDING CHLORO DERIVATIVES THEREOF OR THE N-OXIDES THEREOF

[75] Inventors: Franz Dorn, Dielsdorf; Francois Montavon, Delémont; Milos Suchy, Pfaffhausen, all of Switzerland

[73] Assignee: Hoffmann-La Roche Inc., Nutley, N.J.

[21] Appl. No.: 769,535

[22] Filed: Aug. 26, 1985

Related U.S. Application Data

[62] Division of Ser. No. 412,360, Aug. 27, 1982, Pat. No. 4,556,661.

[30] Foreign Application Priority Data

Sep. 1, 1981 [CH] Switzerland ............... 5622/81
Jul. 9, 1982 [CH] Switzerland ............... 4206/82

[51] Int. Cl.$^4$ .................. C07D 213/26; C07D 213/30; A01N 43/40
[52] U.S. Cl. .................... 514/277; 546/339; 546/344; 546/346
[58] Field of Search ............... 514/277; 546/344, 346, 546/339

[56] References Cited

U.S. PATENT DOCUMENTS 4,431,812  2/1984  Buschmann et al. ............ 546/344
4,556,661 12/1985  Dorn et al. .................... 514/277
4,699,652 10/1987  Zehnder ........................ 71/94

*Primary Examiner*—Alan L. Rotman
*Attorney, Agent, or Firm*—Jon S. Saxe; George M. Gould; Dennis P. Tramaloni

[57] ABSTRACT

Novel pyridine and pyrazine derivatives of the formula

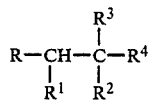

I wherein $R^4$ is 3-pyridyl, 3-pyridyl-1-oxide, 2-pyrazinyl, 2-pyrazinyl-1-oxide, 2-pyrazinyl-4-oxide or 2-pyrazinyl-1,4-dioxide, and R, $R^1$, $R^2$ and $R^3$ are as hereinafter set forth, processes for their preparation, fungicidal compositions containing said compounds, and methods for the use of such compounds or compositions for combatting fungi in agriculture and in horticulture are disclosed. Novel starting materials and fungicidal active substances of the formula

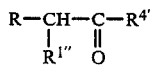

V wherein $R^{4'}$ is 3-pyridyl or 2-pyrazinyl, and R and $R^{1'''}$ as hereinafter set forth, which are used for the preparation of the compounds of formula I, and their N-oxides, as well as fungicidal compositions containing these compounds as the active substance, are also described.

11 Claims, No Drawings

4,753,947

CERTAIN FUNGICIDAL ALPHABENZYL-3-PYRIDYLMETHANOL, THE CORRESPONDING CHLORO DERIVATIVES THEREOF OR THE N-OXIDES THEREOF

This application is a division of application Ser. No. 412,360 filed Aug. 27, 1982, now U.S. Pat. No. 4,556,661.

SUMMARY OF THE INVENTION

This invention relates to novel pyridine and pyrazine derivatives of the formula

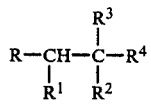

wherein R is phenyl substituted with 1 to 3 halogen atoms, the two ortho-positions not being occupied simultaneously, $R^1$ is halogen, alkyl, $OR^5$, $SR^5$ or $OSO_2R^5$, $R^2$ is hydroxy or chlorine, $R^3$ is hydrogen or alkyl, $R^4$ is 3-pyridyl, 3-pyridyl-1-oxide, 2-pyrazinyl, 2-pyrazinyl-1-oxide, 2-pyrazinyl-4-oxide or 2-pyrazinyl-1,4-dioxide, and $R^5$ is alkyl, with the proviso that when $R^2$ is chlorine and $R^3$ is alkyl, $R^1$ is not bromine or iodine, and acid addition salts of these compounds, and to processes for their preparation.

This invention is also directed to fungicidal compositions containing, as the active ingredient, one of these compounds of formula I and methods for combatting fungi in agriculture and horticulture. Moreover, the invention is concerned with starting materials and fungicidal active substances of the formula

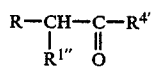

wherein R is as described above, $R^{1''}$ is alkyl and $R^{4'}$ is 3-pyridyl or 2-pyrazinyl, which are used for the preparation of the compounds of formula I, and their N-oxides, as well as fungicidal compositions which contain these compounds as the active ingredient.

DETAILED DESCRIPTION OF THE INVENTION

The present invention comprises heterocyclic compounds, especially pyridine and pyrazine derivatives of formula I

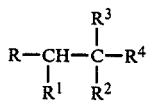

wherein R is phenyl substituted with 1 to 3 halogen atoms, the two ortho-positions not being occupied simultaneously, $R^1$ is halogen, $C_{1-4}$-alkyl, $OR^5$, $SR^5$ or $OSO_2R^5$, $R^2$ is hydroxy or chlorine, $R^3$ is hydrogen or $C_{1-4}$-alkyl, $R^4$ is 3-pyridyl, 3-pyridyl-1-oxide, 2-pyrazinyl, 2-pyrazinyl-1-oxide, 2-pyrazinyl-4-oxide or 2-pyrazinyl-1,4-dioxide and $R^5$ is $C_{1-4}$-alkyl, with the proviso that when $R^2$ is chlorine and $R^3$ is $C_{1-4}$-alkyl, $R^1$ is not bromine or iodine, and acid addition salts thereof.

The compounds of formula I and their acid addition salts possess fungicidal properties and are suitable as fungicidal agents, especially for use in agriculture and in horticulture.

Fungicidal compositions containing compounds of formula I and acid addition salts thereof, as well as methods for their use in combatting plant fungi, are also encompassed within the scope of this invention.

As used herein the term "halogen atom" or "halogen" in the definition of formula I includes fluorine, chlorine, bromine and iodine.

When R is a phenyl group substituted by 2 or 3 halogen atoms, the halogen atoms can be the same or different.

The term "$C_{1-4}$-alkyl" includes not only straight-chain but also branched-chain alkyl groups and, accordingly, the following groups are to be understood: methyl, ethyl, n-propyl, isopropyl, n-butyl, sec.butyl, isobutyl and tert.butyl.

The halogen atoms present in the group R are preferably chlorine atoms. Moreover, R preferably is 2,4-dichlorophenyl.

If $R^1$ is halogen, then this is preferably chlorine or bromine. If $R^1$ is $C_{1-4}$-alkyl, then this is preferably methyl.

$R^3$ preferably is hydrogen or methyl.

Especially preferred compounds of formula I are:
α-(α,2,4-Trichlorobenzyl)-α-methyl-3-pyridylmethanol,
α-(2,4-dichloro-α-methylbenzyl)-3-pyridylmethanol,
α-(α-bromo-2,4-dichlorobenzyl)-α-methyl-2-pyrazinylmethanol and
α-(α-bromo-2,4-dichlorobenzyl)-α-methyl-3-pyridylmethanol.

Other representative compounds of formula I are:
α-(α,2,4-Trichlorobenzyl-3-pyridylmethanol,
α-(α-bromo-2,4-dichlorobenzyl)-3-pyridylmethanol,
α-(2,4-dichloro-α-methoxybenzyl)-3-pyridylmethanol and
α-(2,4-dichloro-α-methoxybenzyl)-α-methyl-2-pyrazinylmethanol.

Since the compounds of formula I contain asymmetric carbon atoms, they can exist as optical antipodes, which are in enantiomeric or diastereomeric relationship to one another. Formula I is, accordingly, intended to include these enantiomeric and diastereomeric forms.

The acid addition salts of the compounds of formula I are physiologically compatible salts. These salts are preferably salts of the compounds of formula I with inorganic and organic acids such as hydrochloric acid; nitric acid; phosphoric acid; mono- and bifunctional carboxylic acids and hydroxycarboxylic acids, such as acetic acid, maleic acid, succinic acid, fumaric acid, tartaric acid, citric acid, salicylic acid, sorbic acid and lactic acid; and sulfonic acids, for example, 1,5-naphthalene-disulfonic acid.

The compounds of formula I and the acid addition salts thereof are prepared by one of the procedures described below.

A. Compounds of formula I, wherein $R^1$ is halogen, $OR^5$, $SR^5$ or $OSO_2R^5$, $R^2$ is hydroxy and $R^4$ is 3-pyridyl or 2-pyrazinyl can be prepared by reacting an epoxide of the formula

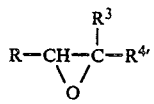

wherein R and $R^3$ are as described above, and $R^{4'}$ is 3-pyridyl or 2-pyrazinyl,
or an alcohol of the formula

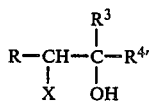

wherein R, $R^3$ and $R^{4'}$ are as described above, and X is an alkylsulfonate group, for example, the methanesulfonate group, or an arylsulfonate group, for example, the benzenesulfonate or p-toluenesulfonate group, with a compound of the formula

wherein $R^{1'}$ is halogen, $OR^5$, $SR^5$ or $OSO_2R^5$, and $R^5$ is as described above.

The reaction is conveniently carried out using an excess of a compound of formula IV and in a temperature range between 0° C. and the reflux temperature of the reaction mixture. When an epoxide of formula II is used, the preferred temperature range is 0° C. to 70° C., and the preferred excess of the compound of formula IV is up to 200 percent by weight. When an alcohol of formula III is used, the reaction is preferably carried out in a temperature range between room temperature and the reflux temperature of the reaction mixture. When an alcohol of formula III is used, the compound of formula IV can also be used in the form of an alkali metal or alkaline earth metal salt.

Moreover, in both cases the reaction can be carried out in a diluent. If a diluent is used, then in the first case this is preferably the reagent Hal-H, $R^5OH$ or $R^5SH$, which is used in excess, or an inert organic solvent, such as an aromatic hydrocarbon, for example, benzene or toluene; an ether or an ether-like compound, for example, diethyl ether, dioxan or tetrahydrofuran; a halogenated aliphatic hydrocarbon, for example, methylene chloride, chloroform or carbon tetrachloride; dimethylformamide; or water. In the second case this is preferably one of the inert organic solvents specified above or water.

In those cases in which the reagent of formula IV itself is not a strong acid, i.e. has a $pK_a$ value higher than about 5, the addition of a mineral acid, for example, sulfuric acid, or a sulfonic acid, for example, p-toluenesulfonic acid, is advantageous for the reaction with an epoxide of formula II. This applies especially when the compound of formula IV is a lower alcohol or a lower mercaptan, i.e. when $R^{1'}$ in formula IV represents $OR^5$ or $SR^5$.

In the reaction with an alcohol of formula III an inversion at the carbon atom carrying the groups R and X takes place, and accordingly, an alcohol of formula III in which X is the group $OSO_2CH_3$ can be reacted with methanesulfonic acid as the compound of formula IV in order to prepare the other enantiomeric form of the alcohol of formula III.

Examples of salts of the compound of formula IV which may be used in this procedure are alkali metal salts, such as the sodium and potassium salts, and alkaline earth metal salts, such as the calcium and magnesium salts.

It has been found to be advantageous to prepare the alcohol of formula III in situ by reacting the corresponding epoxide of formula II with an alkylsulfonic acid or arylsulfonic acid, for example, a compound of formula IV wherein $R^1$ is $OSO_2R^5$, and subsequently to react the resulting alcohol of formula III without isolation with a compound of formula IV or a salt thereof to give the end product.

B. Compounds of formula I wherein $R^1$ is $C_{1-4}$-alkyl, $R^2$ is hydroxy, $R^3$ is hydrogen and $R^4$ is 3-pyridyl or 2-pyrazinyl are prepared by reducing a ketone of the formula

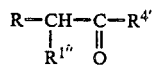

wherein R and $R^{4'}$ are as described above and $R^{1''}$ is $C_{1-4}$-alkyl.

The reduction process is preferably carried out by means of a complex metal hydride, such as sodium borohydride, in a protic diluent, such as an alcohol, for example, methanol or ethanol, at temperatures about room temperature, or lithium aluminium hydride which is used in an aprotic diluent, especially an ether or an ether-like compound, for example, diethyl ether, tetrahydrofuran or dioxan, at temperatures between 0° C. and room temperature. As complex metal hydrides in suitable solvents there also come into consideration lithium borohydride in ethanol or tetrahydrofuran, sodium borohydride/aluminium chloride in an ether (e.g. diglyme) and lithium tri(tert.butoxy)aluminium hydride in tetrahydrofuran. The ketone of formula V can also be reduced to the compound of formula I, for example, using diborane in tetrahydrofuran or by conventional catalytic hydrogenation. The reduction conditions are familiar to one of ordinary skill in the art from analogous reductions.

C. Compounds of formula I wherein $R^1$ is $C_{1-4}$-alkyl, $R^2$ is hydroxy, $R^3$ is $C_{1-4}$-alkyl and $R^4$ is 3-pyridyl or 2-pyrazinyl are prepared by reacting a ketone of formula V, as described above, with a compound of the formula

wherein $R^{3'}$ is $C_{1-4}$-alkyl, Y is lithium or MgZ and Z is halogen, especially bromine or iodine.

The reaction of a ketone of formula V with a compound of formula VI is conveniently carried out in an inert diluent, preferably an aprotic solvent, such as an ether or an ether-like compound, for example, diethyl ether, tetrahydrofuran or dioxan, and in the temperature range between −70° C. and the reflux temperature of the reaction mixture, preferably between −30° C. and room temperature.

D. Compounds of formula I wherein $R^2$ is chlorine and $R^4$ is 3-pyridyl or 2-pyrazinyl are prepared by treating an alcohol of the formula

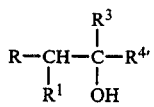   I' wherein R, $R^1$, $R^3$ and $R^{4'}$ are as described above,
or an epoxide of formula II, as defined above, with a chlorinating agent.

The reaction of an alcohol of formula I' is preferably carried out using phosphorus pentachloride, thionyl chloride or phosphorus oxychloride as the chlorinating agent. The reaction is conveniently carried out in the presence of a diluent, especially an inert aprotic organic solvent, and optionally in the presence of a base. Preferred diluents are aliphatic and aromatic hydrocarbons, such as n-hexane, benzene, toluene and xylenes; halogenated aliphatic hydrocarbons, such as methylene chloride, chloroform and carbon tetrachloride; halogenated aromatic hydrocarbons, such as chlorobenzene; and tertiary amines, such as triethylamine and pyridine. Triethylamine, pyridine and calcium carbonate are preferred bases. The reaction temperatures are not critical and can range from 0° C. and the reflux temperature of the reaction mixture, preferably between room temperature and the reflux temperature. The chlorinating agent is preferably used in excess.

The reaction of an epoxide of formula II is conveniently carried out in an excess of chlorinating agent, for example, phosphorus pentachloride, and in the presence of a diluent. Diluents which can be employed in this reaction are inert aprotic organic solvents, such as aliphatic and aromatic hydrocarbons, for example, n-hexane, benzene, toluene and xylenes; and halogenated aliphatic hydrocarbons, for example, methylene chloride, chloroform and carbon tetrachloride. The reaction is preferably carried out at a temperature between 20° C. and the reflux temperature of the reaction mixture.

E. Compounds of formula I wherein $R^1$ is $SR^5$ and $R^2$ is hydroxy can be prepared by reacting a thioether of the formula

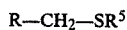   VII wherein R and $R^5$ are as described above,
with an aldehyde or ketone of the formula

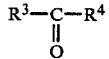   VIII wherein $R^3$ and $R^4$ are as described above.

In this procedure, the thioether of formula VII is conveniently initially reacted with a strong base, such as an alkali metal amide, for example, lithium diisopropylamide, in an inert diluent, such as a hydrocarbon or an ether or an ether-like compound, for example, tetrahydrofuran. Conveniently the reaction temperature is about −70° C. The aldehyde or the ketone of formula VIII is subsequently added, and the reaction mixture is brought to room temperature. In this manner the reaction is normally completed within a short time.

F. Compounds of formula I wherein $R^4$ is 3-pyridyl-1-oxide, 2-pyrazinyl-1-oxide, 2-pyrazinyl-4-oxide or 2-pyrazinyl-1,4-dioxide can be prepared by N-oxidizing a pyridine or pyrazine derivative of the formula

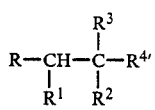   I'' wherein R, $R^1$, $R^2$, $R^3$ and $R^{4'}$ are as described above.

The N-oxidation of those end products of formula I wherein $R^4$ is 3-pyridyl or 2-pyrazinyl is conveniently carried out by treating a compound of formula I'' with hydrogen peroxide or a peracid in the presence of an inert diluent.

When hydrogen peroxide is used as the oxidizing agent, diluents which can be used include lower alkanols, such as methanol, ethanol and isopropanol. The N-oxidation is preferably carried out in a temperature range between 0° and 60° C., especially between 20° and 40° C.

Examples of peracids which can be utilized in this reaction are peracetic acid, perbenzoic acid and m-chloroperbenzoic acid. The N-oxidation is preferably carried out in a halogenated hydrocarbon, for example, methylene chloride or chloroform, as the diluent.

The temperature range of the N-oxidation reaction with a peracid is not critical and can be from 0° C. to the reflux temperature of the reaction mixture. The preferred range is from 0° C. to room temperature. An especially preferred embodiment of this process comprises carrying out the N-oxidation with m-chloroperbenzoic acid in chloroform in a temperature range between 0° C. and room temperature.

The acid addition salts of the compounds of formula I are conveniently prepared by reacting the compounds of formula I with the desired acids in the usual manner.

The isolation and purification of compounds of formula I or of the acid addition salts can be carried out using conventional procedures.

The epoxides of formula II used as starting materials are novel. They can be prepared by reacting a halide of the formula

   IX wherein R is as previously described and Hal is chlorine, bromine or iodine,
with an aldehyde or ketone of formula VIII, as previously described, and with dimethyl sulfide in aqueous medium.

This reaction is conveniently carried out as a one-pot process in the presence of an inert organic solvent and a base. Accordingly, it is preferably carried out in an aqueous-organic system. Suitable organic solvents are aliphatic and aromatic hydrocarbons, such as n-hexane, benzene and toluene; alcohols, such as methanol, ethanol and isopropanol; and ethers and ether-like compounds, such as diethyl ether, tetrahydrofuran and dioxan. Preferred bases are water-soluble alkali hydroxides, such as sodium hydroxide and potassium hydroxide. The reaction is conveniently carried out at a temperature between room temperature and the reflux temperature of the reaction mixture.

Some of the starting materials of general formula III correspond to those compounds of formula I wherein $R^1$ is $OSO_2R^5$, $R^2$ is hydroxy and $R^4$ is 3-pyridyl or 2-pyrazinyl. Such compounds can be prepared, for example, by reacting an epoxide of formula II with an alkanesulfonic acid or an aromatic sulfonic acid in accordance with or in an analogous manner to procedure A.

The starting materials of general formula V are novel and can be prepared by treating a ketone of the formula

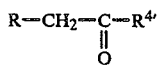   X wherein R and R$^{4'}$ are as previously described, with an alkylating agent of the formula $R^{1''}$—U   XI wherein R$^{1''}$ is as previously described and U is a leaving group, especially chlorine, bromine or iodine.

In this reaction, the ketone of formula X is advantageously converted with a base, such as sodium hydride or lithium diisopropylamide, in a diluent at reaction temperatures between −70° C. and 50° C. into an anion which is then treated with the alkylating agent of formula XI. Diluents which can be used in this reaction are aprotic organic solvents, such as tetrahydrofuran, dimethoxyethane, dimethylformamide, and the like.

The starting materials of general formula VI are either known or can be prepared according to known methods.

The starting materials of formula I' correspond to those compounds of formula I where R$^2$ is hydroxy and R$^4$ is 3-pyridyl or 2-pyrazinyl. These compounds can be prepared, for example, in accordance with or in an analogous manner to those of procedures A, B, C and E above.

The starting materials of formulae VII, VIII, IX and XI are either known or can be prepared according to known methods.

The ketones of general formula X which are used as starting materials are either known or can be prepared according to known methods, see, for example, German Offenlegungsschrift No. 2 221 546. However, the following process is especially preferred:

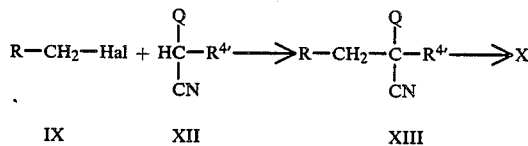

wherein R, R$^{4'}$ and Hal are as described above and Q is a disubstitued amino group, for example, dimethylamino, diethylamino, piperidino or morpholino.

The reaction of a compound of formula IX with a compound of formula XII can be carried out, for example, under the phase-transfer catalysis conditions, as described by J. Dockx, Synthesis (1973), 441. The reaction can also be carried out using a base, such as, for example, sodium hydride or lithium diisopropylamide in an inert solvent, such as an ether or an ether-like compound, for example, tetrahydrofuran or dimethoxyethane, in a temperature range between −70° C. and 50° C., preferably between −30° C. and room temperature, and with the exclusion of water. The compound of formula XIII can thereupon be converted into the ketone of formula X by hydrolysis, for example, by conventional treatment with an aqueous acid. Examples of acids which can be used for this reaction include strong inorganic acids, such as sulfuric acid, hydrochloric acid and hydrobromic acid as well as sulfonic acids, such as benzenesulfonic acid and p-toluenesulfonic acid. The hydrolysis is conveniently carried out in a temperature range between 20° C. and the reflux temperature of the reaction mixture, preferably between 80° C. and 100° C.

The compounds of formula I and their acid addition salts possess fungicidal activity and can accordingly be used for combatting fungi in agriculture and in horticulture. They are especially suitable for eliminating or combatting phytopathogenic fungi on parts of plants, for example, leaves, stems, roots, tubers, fruits or flowers, on seeds as well as in the soil.

The compounds of formula I are especially effective against Botrytis cinerea (grey mould); powdery mildew fungi, such as, for example, Uncinula necator (powdery mildew of vines), Erysiphe cichoracearum (powdery mildew of cucumbers), Podosphaera leucotricha (powdery mildew of apples) and Erysiphe graminis (powdery mildew of cereals); Venturia inaequalis (apple scab); Helminthosporium oryzae (brown spot disease of rice); and harmful fungi of the genera Puccinia, Uromyces, Hemileia, Rhizoctonia, Penicillium, Septoria, Corticium and Cercospora.

Furthermore, certain compounds of formula I possess a pronounced activity against wood-destroying fungi, such as, for example, Coniophora puteana and Gloeophyllum trabeum.

The compounds of formula I of the present invention possess local and/or systemic activity.

The compounds of formula I are active under greenhouse conditions even at a concentration of 1 mg to 500 mg of active ingredient per liter of spray liquor. In the open air, they are advantageously applied in concentrations of 25 g to 1000 g of active ingredient of formula I per hectare and treatment. For control of seed-borne fungi, 0.05 g to 1.5 g of active ingredient of formula I per kg of seeds are advantageously applied in a disinfecting process.

The aforementioned ketones of formula V, as well as their N-oxides, are also valuable as fungicides, since they have a similar spectrum of activity as the compounds of formula I. These ketones and their N-oxides can accordingly also be used for combatting fungi in agriculture and in horticulture, namely in the same manner as the compounds of formula I. The N-oxides can be prepared by N-oxidizing the ketones of formula V, namely in an analogous manner to procedure F above.

The invention is also directed to fungicidal compositions which comprise inert carrier material and, as the active ingredient, an effective amount of a compound of formula I or an acid addition salt thereof. These fungicidal compositions contain, as the inert carrier material, at least one of the following ingredients: solid carrier materials; solvents or dispersion media; surface active agents, for example, wetting and emulsifying agents; dispersing agents; and stabilizers.

Examples of solid carrier materials include natural mineral substances, such as kaolin, aluminas, siliceous earth, talc, bentonite, chalk, magnesium carbonate, limestone, quartz, dolomite, attapulgite, montmorillonite and diatomaceous earth; synthetic mineral substances, such as highly dispersible silicic acid, aluminium oxide and silicates; organic substances, such as cellulose, starch, urea and synthetic resins; and fertilizers, such as phosphates and nitrates, whereby such carrier substances can be present, for example, as dusts, powders or granulates.

Examples of liquid solvents or dispersion media include: aromatics, such as benzene, toluene, xylenes and alkylnaphthalenes; chlorinated aromatics and chlorinated aliphatic hydrocarbons, such as chlorbenzenes, chloroethylenes and methylene chloride; aliphatic hydrocarbons, such as cyclohexane and paraffins (e.g., petroleum fractions); alcohols, such as butanol and glycol, as well as their ethers and esters; ketones, such as acetone, methyl ethyl ketone, methyl isobutyl ketone and cyclohexanone; strongly polar solvents or dispersion media, such as dimethylformamide, N-methylpyrrolidone and dimethylsulfoxide, whereby such solvents or dispersion media preferably have flash points of at least 30° C. and boiling points of at least 50° C., and water. When water is used as the solvent, organic solvents can also be used as auxiliary solvents.

Included among the solvents or dispersion media are the so-called liquified gaseous extenders or carrier substances. By liquified gaseous extenders or carrier substances are meant liquids which are gaseous at normal temperature and under normal pressure, such as aerosol propellants, e.g., halogenated hydrocarbons (e.g., dichlorodifluoromethane).

Surface active agents, especially emulsifying agents and wetting agents, suitable for use in the fungicidal compositions of this invention can be non-ionic, anionic or cation compounds.

Examples of non-ionic compounds which can be used include condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

Examples of anionic compounds include soaps; fatty sulfate esters, such as dodecyl sodium sulfate, octadecyl sodium sulfate and cetyl sodium sulfate; alkyl sulfonates, aryl sulfonates, and fatty-aromatic sulfonates, such as alkylbenzene sulfonates, for example, calcium dodecylbenzene sulfonate, and butylnaphthalene sulfonates; and more complex fatty sulfonates, for example, the amide condensation products or oleic acid and N-methyltaurine and the sodium sulfonate or dioctyl succinate.

Examples of cationic compounds include alkyldimethylbenzylammonium chlorides, dialkyldimethylammonium chlorides, alkyltrimethylammonium chlorides and ethoxylated quaternary ammonium chlorides.

Dispersing agents suitable for use in the fungicidal compositions of this invention are lignin, sodium and ammonium salts of lignin sulfonic acid, sodium salts of maleic acid anhydride-diisobutylene copolymers, sodium and ammonium salts of sulfonated polycondensation products of naphthalene and formaldehyde, and sulfite lyes. Dispersing agents, which are especially suitable as thickening or anti-settling agents, include methylcellulose, carboxymethylcellulose, hydroxyethylcellulose, polyvinyl alcohol, alginates, caseinates and blood albumin.

Stabilizers suitable for use in the fungicidal compositions of the present invention include acid-binding agents, such as epichlorohydrin, phenyl glycidyl ether and soya epoxides; antioxidants, such as gallic acid esters and butylhydroxytoluene; UV-absorbers, such as substituted benzophenones, diphenylacrylonitrile acid esters and cinnamic acid esters; and deactivators, such as salts of ethylenediaminotetraacetic acid and polyglycols.

The fungicidal compositions of this invention can contain, in addition to the active substances of formula I, other active substances, such as other fungicidal agents, insecticidal and acaricidal agents, bactericides, plant growth regulators and fertilizers. Such combination compositions are suitable for increasing the activity or for broadening the spectrum of activity and for specifically influencing plant growth.

The fungicidal compositions of the present invention can be prepared by known methods, for example, by mixing the active ingredient with solid carrier materials, by dissolution or suspension in suitable solvents or dispersion media, and, if necessary, using surface active agents, as wetting or emulsifying agents, or dispersing agents, or by diluting pre-prepared emulsifiable concentrates with solvents or dispersion media.

In preparing the fungicidal compositions of the present invention, the active ingredient of formula I is mixed with inert carrier material. In the case of pulverous composition, the active ingredient can be mixed with the solid carrier material, for example, by milling together, or the solid carrier material can be impregnated with a solution or suspension of the active ingredient and then the solvent or suspension medium can be removed by evaporation, heating or removing under reduced pressure. By the addition of surface active or dispersing agents, such pulverous compositions can be made readily wettable with water so that they can be converted into aqueous suspensions which are suitable, for example, as spray compositions.

The compounds of formula I can be mixed with a surface active agent and a solid carrier material to form a wettable powder which is dispersible in water, or they can be mixed with a solid pre-granulated carrier material to form a granulate.

For preparation of emulsifiable concentrates which are especially suitable for storage and shipment, the active ingredient can be dissolved in a water-immiscible solvent, such as, for example, an alicyclic ketone, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active substance can be dissolved in a solvent, and thereafter the solution can be mixed with an emulsifying agent. Such a mixture can likewise be diluted with water to the desired concentration. In this manner there are obtained emulsifiable concentrates or ready-for-use emulsions.

The fungicidal compositions of this invention generally contain between 0.0001 percent by weight and 95 percent by weight of compound or compounds of formula I as active ingredient.

The fungicidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range. Emulsifiable concentrates generally contain from about 5 percent by weight to about 95 percent by weight, preferably from 25 percent by weight to 75 percent by weight, of the compound or compounds of formula I.

The application forms prepared from the above-indicated compositions include ready-for-use solutions, emulsions, foams, suspensions, powders, pastes, soluble powders, dusting agents and granulates.

The concentrations of active ingredient in the ready-for-use preparations can vary over wide limits. In spray liquors, the concentration can be, for example, between 0.0001 percent by weight and 20 percent by weight.

The active ingredients can also be used with good effect in the Ultra-Low-Volume process (ULV) where it is possible to formulate spray liquors having preferably from about 0.05 to about 20 percent by weight of active ingredient.

The active ingredients can also be used with good effect in the Low-Volume process and in the High-Volume process where it is possible to formulate spray liquors having from 0.02 to 1.0 and 0.002 to 0.1 percent by weight of active ingredient respectively.

The present invention is also concerned with a method for combatting fungi by employing conventional application methods used in plant protection or in agriculture. This method comprises treating the locus to be protected, for example, plants, parts of plants or seeds, with an effective amount of a compound of formula I, an acid addition salt thereof, or a composition containing such compounds.

The following Examples illustrate the invention:

I MANUFACTURE OF THE ACTIVE SUBSTANCES OF FORMULA I

EXAMPLE 1

14 g of cis-1-(2,4-dichlorophenyl)-2-(3-pyridyl)-1,2-epoxypropane are dissolved in 35 ml of concentrated hydrochloric acid at 0°–5° C. while stirring. The solution is then stirred in this temperature range for an additional 4 hours and subsequently poured into ice/water. The resulting crystals are filtered off, washed first with water and then with diethyl ether and dried. After recrystallization of the resulting crude product (14 g dry weight) it is recrystallized from methylene chloride/diethyl ether and finally washed with diethyl ether to yield 9.4 g of α-(α,2,4-trichlorobenzyl)-α-methyl-3-pyridylmethanol in the form of the threo isomer, m.p. 148°–149.5° C.

In an analogous manner there is obtained:

(a) From cis 1-(2,4-dichlorophenyl)-2-(3-pyridyl)-1,2-epoxypropane and concentrated hydrobromic acid, α-(α-bromo-2,4-dichlorobenzyl)-α-methyl-3-pyridylmethanol in the form of the threo isomer, m.p. 151° C. (with decomposition).

(b) From 1-(2,4-dichlorophenyl)-2-(3-pyridyl)-1,2-epoxypropane and methanol with addition of concentrated sulfuric acid, α-(2,4-dichloro-α-methoxybenzyl)-α-methyl-3-pyridylmethanol as a diastereomeric mixture, m.p. 109°–113° C.

(c) From 1-(2,4-dichlorophenyl)-2-(3-pyridyl)-1,2-epoxypropane and methanesulfonic acid in methylene chloride, 2,4-dichloro-α-[1-hydroxy-1-(3-pyridyl)-ethyl]-benzyl methanesulfonate as a diastereomeric mixture, m.p. 137°–141° C. By chromatography on silica gel there are obtained two isomers of m.p. 141°–143° C. and 159°–162° C., respectively.

(d) From 1-(2,4-dichlorophenyl)-2-(2-pyrazinyl)-1,2-epoxypropane and methanesulfonic acid, 2,4-dichloro-α-[1-hydroxy-1-(2-pyrazinyl)-ethyl)-benzyl methanesulfonate as a highly viscous oil.

EXAMPLE 2

168.5 g of cis-1-(2,4-dichlorophenyl)-2-(3-pyridyl)-1,2-epoxypropane in 160 ml of methylene chloride are treated with 150 ml of methanesulfonic acid and the mixture is refluxed at 45° C. for 5 hours. After cooling there are added to the mixture 130 g of ammonium chloride and 900 ml of concentrated hydrochloric acid and then the mixture is stirred at room temperature for 115 hours. The hydrochloric acid is then distilled off by means of a water-jet vacuum, the residue is dissolved in water and the resulting solution is neutralized with 300 g of sodium carbonate. The mixture is extracted with ethyl acetate, and the organic phase is dried over anhydrous magnesium sulfate. After evaporating the solvent, the crude product (230 g; solvent-moist; about 60% of erythro isomer and 40% of threo isomer) is crystallized from toluene (fractional crystallization). The product consists of α-(α,2,4-trichlorobenzyl)-α-methyl-3-pyridylmethanol as the erythro isomer, m.p. 135°–137° C. (65 g), threo isomer, m.p. 148°–149.5° C. (24 g) and diastereoisomeric mixture (about 1:1; 85 g).

In an analogous manner there is obtained:

(a) From 1-(2,4-dichlorophenyl)-2-(3-pyridyl)-1,2-epoxybutane, methanesulfonic acid and concentrated hydrochloric acid, α-(α,2,4-trichlorobenzyl)-α-ethyl-3-pyridylmethanol as a diastereomeric mixture. By chromatography on silica gel there is obtained a purer product, m.p. 162–164° C.

(b) From 1-(2,4-dichlorophenyl)-2-(2-pyrazinyl)-1,2-epoxypropane, methanesulfonic acid and concentrated hydrochloric acid, α-(α,2,4-trichlorobenzyl)-α-methyl-2-pyrazinylmethanol as a diastereomeric mixture. By chromatography on silica gel there are obtained two isomers, the one of m.p. 133°–134° C. and the other as a highly viscous oil.

(c) From 1-(2,4-dichlorophenyl)-2-(2-pyrazinyl)-1,2-epoxypropane, methanesulfonic acid and concentrated hydrobromic acid, α-(α-bromo-2,4-dichlorobenzyl)-α-methyl-2-pyrazinylmethanol as a diastereomeric mixture. By chromatography on silica gel there are obtained two isomers, the one of m.p. 116°–117° C. and the other of m.p. 135°–136° C.

(d) From 1-(2,4-dichlorophenyl)-2-(2-pyrazinyl)-1,2-epoxypropane, methanesulfonic acid and concentrated hydroiodic acid, α-(α-iodo-2,4-dichlorobenzyl)-α-methyl-2-pyrazinylmethanol which is separated into two diastereomers, the one of m.p. 183°–185° C. and the other of m.p. 152°–153° C.

(e) From cis-1-(2,4-dichlorophenyl)-2-(3-pyridyl)-1,2-epoxypropane, methanesulfonic acid and concentrated hydrobromic acid, α-(α-bromo-2,4-dichlorobenzyl)-α-methyl-3-pyridylmethanol as a diastereomeric mixture. By chromatography on silica gel there is obtained the threo isomer, m.p. 154° C. (with decomposition), and the erythro isomer, m.p. 135°–136° C.

EXAMPLE 3

2.5 g of 2-(2,4-dichlorophenyl)-1-(3-pyridyl)-1-propanone are dissolved in 10 ml of methanol and treated with 0.4 g of sodium borohydride. After a reaction time of 3 hours at room temperature, the mixture is poured into ice/water and the resulting mixture is extracted with diethyl ether. The organic phase is washed, dried over anhydrous sodium sulfate and the solvent is removed under reduced pressure. After crystallization of the residue from ethyl acetate/n-hexane there is obtained α-(2,4-dichloro-α-methylbenzyl)-3-pyridylmethanol, m.p. 94°-96° C.

In an analogous manner, by reducing 2-(2,4-dichlorophenyl)-1-(3-pyridyl)-1-butanone using sodium borohydride as the reducing agent there is obtained α-(2,4-dichloro-α-ethylbenzyl)-3-pyridylmethanol as a viscous oil.

EXAMPLE 4

A solution of 2 g of 2-(2,4-dichlorophenyl)-1-(3-pyridyl)-1-propanone in 10 ml of diethyl ether is added dropwise at room temperature to a Grignard reagent prepared from 0.26 g of magnesium shavings and 1.5 g of methyl iodide in 15 ml of diethyl ether. After a reaction time of 1 hour at room temperature the mixture is poured into water and the resulting mixture is extracted with diethyl ether. The organic phase is washed, dried over anhydrous sodium sulfate and the solvent is removed under reduced pressure. There is obtained α-(2,4-dichloro-α-methylbenzyl)-α-methyl-3-pyridylmethanol, m.p. 111°-113° C.

In an analogous manner there is obtained:

(a) From ethylmagnesium bromide and 2-(2,4-dichlorophenyl)-1-(3-pyridyl)-1-propanone, α-(2,4-dichloro-α-methylbenzyl)-α-ethyl-3-pyridylmethanol as a viscous oil.

(b) From methylmagnesium iodide and 2-(2,4-dichlorophenyl)-1-(3-pyridyl)-1-butanone, α-(2,4-dichloro-α-ethylbenzyl)-α-methyl-3-pyridylmethanol, m.p. 55°-56° C.

EXAMPLE 5

11.2 g of cis-1-(2,4-dichlorophenyl)-2-(3-pyridyl)-1,2-epoxypropane are dissolved in 40 ml of absolute toluene. The solution is treated while stirring with 17 g of phosphorus pentachloride, left to stand for 16 hours and thereafter stirred at 85° C. for an additional 45 minutes. After cooling, the reaction mixture is poured into ice-/water/methylene chloride. The resulting two-phase reaction mixture is neutralized with 70 g of sodium bicarbonate, the organic phase is separated and the aqueous phase is extracted with methylene chloride. The combined organic solutions are subsequently dried over anhydrous sodium sulfate and thereupon concentrated. By chromatography of the residue on silica gel (eluant: diethyl ether/cyclohexane) and crystallization from n-pentane there are obtained 9.2 g of α-(α,2,4-trichlorobenzyl)-α-methyl-3-pyridylmethyl chloride as a 3:1 diastereomeric mixture, m.p. 55°-65° C. By chromatography on silica gel with toluene/acetic acid (4:1) there are obtained two isomers, m.p. 68.5°-69° C. and 71°-73° C., respectively.

In an analogous manner there is obtained by chlorinating 1-(2,4-dichlorophenyl)-2-(2-pyrazinyl)-1,2-epoxypropane with phosphorus pentachloride α-(α,2,4-trichlorobenzyl)-α-methyl-3-pyridylmethyl chloride as an oil.

EXAMPLE 6

10 g of α-(2,4-dichloro-α-methylbenzyl)-3-pyridylmethanol are stirred at 85° C. for 90 minutes in 25 ml of phosphorus oxychloride. The mixture is then poured on to ice and neutralized by adding sodium bicarbonate. The crude product obtained by extraction with ethyl acetate is chromatographed on silica gel. 3(α,2,4-Trichloro-β-methylphenethyl)pyridine is eluted with n-hexane/ethyl acetate in the form of an oil.

EXAMPLE 7

3 g of 2,4-dichlorobenzyl methyl sulfide are added to a solution of lithium diisopropylamide (prepared from 1.6 g of diisopropylamine and an equivalent amount of n-butyl lithium) in 10 ml of tetrahydrofuran at −70° C. and the mixture is allowed to react at this temperature for 1 hour. 1.81 g of pyridine-3-carbaldehyde are then added thereto and the mixture is left to warm slowly to room temperature. The mixture is treated with water and extracted with diethyl ether. The product is chromatographed on silica gel with ethyl acetate. There is obtained α-[2,4-dichloro-α-(methylthio)-benzyl]-3-pyridylmethanol as a diastereomeric mixture which has a m.p. of 98°-104° C. after one recrystallization from ethyl acetate/n-hexane.

In an analogous manner there is obtained:

(a) From 2,4-dichlorobenzyl methyl sulfide and 3-acetylpyridine, α-[2,4-dichloro-α-(methylthio)-benzyl]-α-methyl-3-pyridylmethanol, m.p. 130°-136° C.

(b) From 2,4-dichlorobenzyl methyl sulfide and 2-acetylpyrazine, α-[2,4-dichloro-α-(methylthio)-benzyl]-α-methyl-2-pyrazinylmethanol as an oil.

EXAMPLE 8

6 g of α-(2,4-dichloro-α-methylbenzyl)-3-pyridylmethanol are dissolved in 200 ml of chloroform and treated at 0° C. with 3.96 g of 3-chloroperbenzoic acid. The mixture is then left to react at about 4° C. for 16 hours. The mixture is poured into 5% sodium carbonate solution and subsequently extracted with chloroform. Upon concentrating the solution there are obtained white crystals of α-(2,4-dichloro-α-methylbenzyl)-3-pyridylmethanol-1-oxide, m.p. 167°-170° C.

In an analogous manner there is obtained from α-(α,2,4-trichlorobenzyl)-α-methyl-3-pyridylmethanol and 3-chloro-perbenzoic acid α-(α,2,4-trichlorobenzyl)-α-methyl-3-pyridylmethanol-1-oxide, m.p. 63°-68° C.

II PREPARATION OF THE STARTING MATERIALS

EXAMPLE 9

The epoxides of formula II which are used as the starting materials in Examples 1, 2 and 5 can be prepared as follows:

140 g of 2,4-dichlorobenzyl chloride are suspended in 200 ml of water and treated with 60 ml of dimethyl sulfide. The mixture is then stirred for 20 hours at a bath temperature of 35°-40° C.

An intensive cooler is used and the mixture is cooled by means of methanol at −10° C. After a reaction time of 20 hours there are added to the sulfonium salt formed 200 ml of 3-acetylpyridine, 61 g of potassium hydroxide in 100 ml of water and 200 ml of n-hexane. The suspension is stirred at 50°-60° C. (bath temperature) for 2 hours.

The aqueous layer is separated and the hexane phase is washed twice with 100 ml of water, dried over anhydrous sodium sulfate and thereupon concentrated. The residue is subjected to column chromatography. There is obtained cis-1-(2,4-dichlorophenyl)-2-(3-pyridyl)-1,2-epoxypropane, m.p. 68°-70° C., and trans-1-(2,4-dichlorophenyl)-2-(3-pyridyl)-1,2-epoxypropane, m.p. 102°-103° C.

In an analogous manner there is obtained:

(a) From 2,4-dichlorobenzyl chloride, 3-pyridinealdehyde and dimethyl sulfide, 1-(2,4-dichlorophenyl)-2-(3-pyridyl)-1,2-epoxyethane, m.p. 70°–74° C.

(b) From 2,4-dichlorobenzyl chloride, 3-propionylpyridine and dimethyl sulfide, 1-(2,4-dichlorophenyl)-2-(3-pyridyl)-1,2-epoxybutane, $n_D^{20}$ 1.5683.

(c) From 2,4-dichlorobenzyl chloride, 2-acetylpyrazine and dimethyl sulfide, 1-(2,4-dichlorophenyl)-2-(2-pyrazinyl)-1,2-epoxypropane, m.p. 107°–109° C.

EXAMPLE 10

The ketones of formula V which are used as the starting materials in Examples 3 and 4 can be prepared as follows:

28 g of 2,4-dichlorobenzyl 3-pyridyl ketone are dissolved in 800 ml of dimethylformamide and treated portionwise at 0° C. with 5.5 g of sodium hydride (50% dispersion in oil). After 2 hours at room temperature 14.9 g of methyl iodide are added and the mixture is stirred at room temperature for a further 3 hours. The mixture is then poured into water and extracted with diethyl ether. The organic phase is washed, dried over anhydrous sodium sulfate and subsequently concentrated. By chromatography on silica gel with n-hexane/ethyl acetate (1:2) there is obtained 2-(2,4-dichlorophenyl)-1-(3-pyridyl)-1-propanone as an oil.

In an analogous manner there is obtained:

(a) From 2,4-dichlorobenzyl 3-pyridyl ketone and ethyl bromide, 2-(2,4-dichlorophenyl)-1-(3-pyridyl)-1-butanone as an oil.

(b) From 2,4-dichlorobenzyl 3-pyridyl ketone and isopropyl bromide, 2-(2,4-dichlorophenyl)-3-methyl-1-(3-pyridyl)-1-butanone as an oil.

(c) The 2,4-dichlorobenzyl 3-pyridyl ketone which is used as the starting material above can be prepared as follows:

125 g of 2,4-dichlorobenzyl chloride are added at room temperature to a mixture of 700 g of 50% sodium hydroxide, 23 g of tetrabutylammonium iodide and 130 g of α-(3-pyridyl)-α-(4-morpholino)-acetonitrile. After 2 hours the mixture is extracted with diethyl ether. After evaporation of the ether there remains behind as the crude product α-(2,4-dichlorobenzyl)-α-(3-pyridyl)-4-morpholino-acetonitrile (m.p. 130°–132° C.). This is taken up in 300 ml of concentrated hydrochloric acid and the solution is heated to reflux temperature for 12 hours. It is then basified and extracted with ethyl acetate, and the organic phase is washed, dried over anhydrous sodium sulfate and concentrated. From ethyl acetate/n-hexane there is obtained 2,4-dichlorobenzyl 3-pyridyl ketone, m.p. 78°–79° C.

III. FORMULATION EXAMPLES

EXAMPLE 11

This Example illustrates the preparation of spray powders using the compounds of formula I as the active ingredient.

1. Spray powder for active ingredients of formula I which are liquid or which melt below 75° C.

| Ingredient | Parts by weight |
|---|---|
| Active substance of formula I or V | 50 |
| Hydrated silicic acid | 37 |
| Kaolin | 5 |
| Alkylphenol ethoxylate | 4 |
| Sodium polynaphthalenesulfonate | 4 |

| Ingredient | Parts by weight |
|---|---|
| | 100 |

The liquid or molten active ingredient is taken up on the silicic acid, the remaining components are admixed and the mixture is finely ground in a suitable mill.

2. Spray powder for solid active ingredients of formula I which melt about 75° C.

| Ingredient | Parts by weight |
|---|---|
| Active substance of formula I or V | 50 |
| Hydrated silicic acid | 5 |
| Kaolin | 42 |
| Sodium lauryl sulfate | 1 |
| Sodium lignosulfonate | 2 |
| | 100 |

The components are mixed with one another and the mixture is finely ground in a suitable mill.

EXAMPLE 12

This Example illustrates the preparation of an emulsifiable concentrate using compounds of formula I which are liquid at 20°–25° C. by admixture of the following ingredients.

| Ingredient | Parts by weight |
|---|---|
| Active substance of formula I or V | 500 |
| Castor oil ethoxylate | 100 |
| Calcium dodecylbenzenesulfonate | 25 |
| Mixture of $C_{10}$—alkylbenzenes | ad 1000 parts by volume |

The components are mixed with one another until a clear solution is obtained.

We claim:

1. A compound of the formula

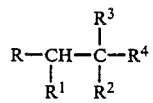

wherein R is phenyl substituted with 1 to 3 halogen atoms, the two ortho-positions not being occupied simultaneously, $R^1$ is halogen, $C_{1-4}$-alkyl, $OR^5$, $SR^5$ or $OSO_2R^5$, $R^2$ is hydroxy or chlorine, $R^3$ is hydrogen, $R^4$ is 3-pyridyl, 3-pyridyl-1-oxide and $R^5$ is $C_{1-4}$-alkyl, and an acid addition salt thereof.

2. The compound according to claim 1, wherein $R^4$ is 3-pyridyl.

3. The compound according to claim 1 or claim 2, wherein R is 2,4-dichlorophenyl.

4. α-(2,4-Dichloro-α-methylbenzyl)-3-pyridylmethanol.

5. The compound according to claim 2 which is α-[2,4-dichloro-α-(methylthio)-benzyl]-3-pyridylmethanol.

6. The compound according to claim one which is: α(2,4-dichloro-α-ethylbenzyl)-3-pyridylmethanol, or α-(2,4,-dichloro-α-methylbenzyl)-3-pyridylmethanol-1-oxide.

7. A fungicidal composition comprising a compatible carrier material and, as the active ingredient, an amount which is effective as a fungicide of a compound of the formula

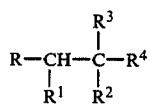

wherein R is phenyl substituted with 1 to 3 halogen atoms, the two ortho-positions not being occupied simultaneously, $R^1$ is halogen, $C_{1-4}$-alkyl, $OR^5$, $SR^5$ or $OSO_2R^5$, $R^2$ is hydroxy or chlorine, $R^3$ is hydrogen, $R^4$ is 3-pyridyl, 3-pyridyl-1-oxide and $R^5$ is $C_{1-4}$-alkyl, and an acid addition salt thereof.

8. The fungicidal composition of claim 11, wherein $R^4$ is 3-pyridyl.

9. The fungicidal composition of claim 8 comprising an effective amount of α-(2,4-dichloro-α-methylbenzyl)-3-pyridylmethanol.

10. A method for combatting fungi in agriculture and in horticulture, which comprises applying to the locus to be protected an effective amount of a composition of claim 7.

11. The method of claim 10 wherein the composition comprises an effective amount of α-(2,4-dichloro-α-methylbenzyl)-3-pyridylmethanol.

* * * * *